United States Patent [19]
White

[11] Patent Number: 5,924,862
[45] Date of Patent: Jul. 20, 1999

[54] METHOD AND APPARATUS TO VERIFY DENTAL MODEL ACCURACY

[76] Inventor: Dennis J White, 51 Nostrand Rd., Cranbury, N.J. 08512

[21] Appl. No.: 08/959,484

[22] Filed: Oct. 28, 1997

[51] Int. Cl.[6] ................................................ A61C 8/00
[52] U.S. Cl. ........................ 433/72; 600/590; 33/513; 33/544.5
[58] Field of Search .................... 433/72–76; 33/456, 33/460, 473, 501.17, 513, 514, 544.5, 557, 558.2, 558.5, 560, 512, 561.1, 562; 600/589, 590

[56] References Cited

U.S. PATENT DOCUMENTS

| | | | |
|---|---|---|---|
| 82,214 | 9/1868 | Ferren | 33/195 |
| 386,004 | 7/1888 | Eddy . | |
| 655,933 | 8/1900 | Le Cron | 433/76 |
| 1,216,596 | 2/1917 | Nishi | 433/75 |
| 1,385,070 | 7/1921 | Davison . | |
| 1,581,913 | 4/1926 | Bonoff | 33/513 |
| 2,309,270 | 1/1943 | Opotow . | |
| 2,410,686 | 11/1946 | Sayward | 33/558.2 |
| 2,419,597 | 4/1947 | Rushmore | 33/279 |
| 2,457,090 | 12/1948 | Ringle et al. | 433/75 |
| 3,200,497 | 8/1965 | Goodfriend . | |
| 3,879,849 | 4/1975 | Schwartz et al. | 600/589 |
| 4,229,166 | 10/1980 | Cusato et al. | 433/72 |
| 4,964,769 | 10/1990 | Hass | 433/69 |
| 5,580,244 | 12/1996 | White | 433/37 |
| 5,722,832 | 3/1998 | White | 433/214 |

FOREIGN PATENT DOCUMENTS 4115335  11/1992  Germany .

*Primary Examiner*—Ralph A. Lewis

[57] ABSTRACT

A methods and apparatus is disclosed herein that confirms the accuracy of dental casts. The device has four adjustable arms terminating in rests. The rests are slightly concave to receive methylmethacrylate. The arms are adjustable to mate rests with selected points or cusp tips on the model. In use, the set screw is loosened to allow a friction fit adjustment of the four arms. Once the four arms are adjusted so that the rests are aligned over desired cusp tips a locking screw is tightened. The arms are held immobilized. Methylmethacrylate is now added to the concave portion of rests. While this acrylic is still soft it is returned in the same location on model to register the imprint of the preselected cusp tips. The verifier can now be utilized to verify accuracy of another clone model by placing in similar manner on second cast. The verifier should come to rest on the second model exactly as it did on the original.

2 Claims, 3 Drawing Sheets

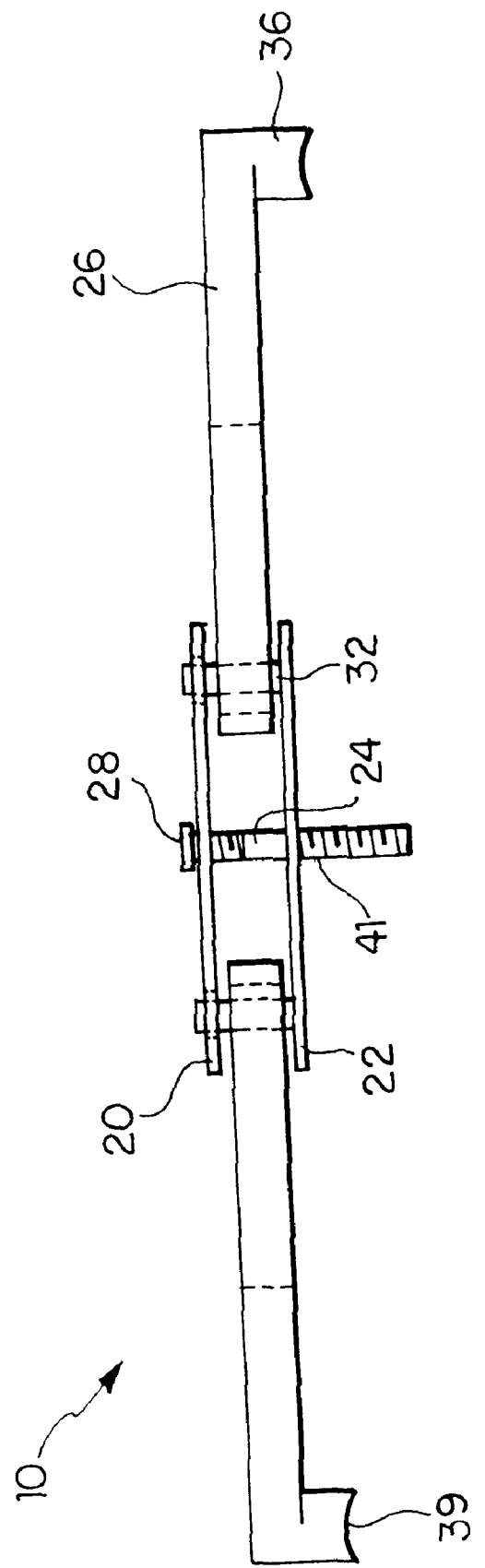

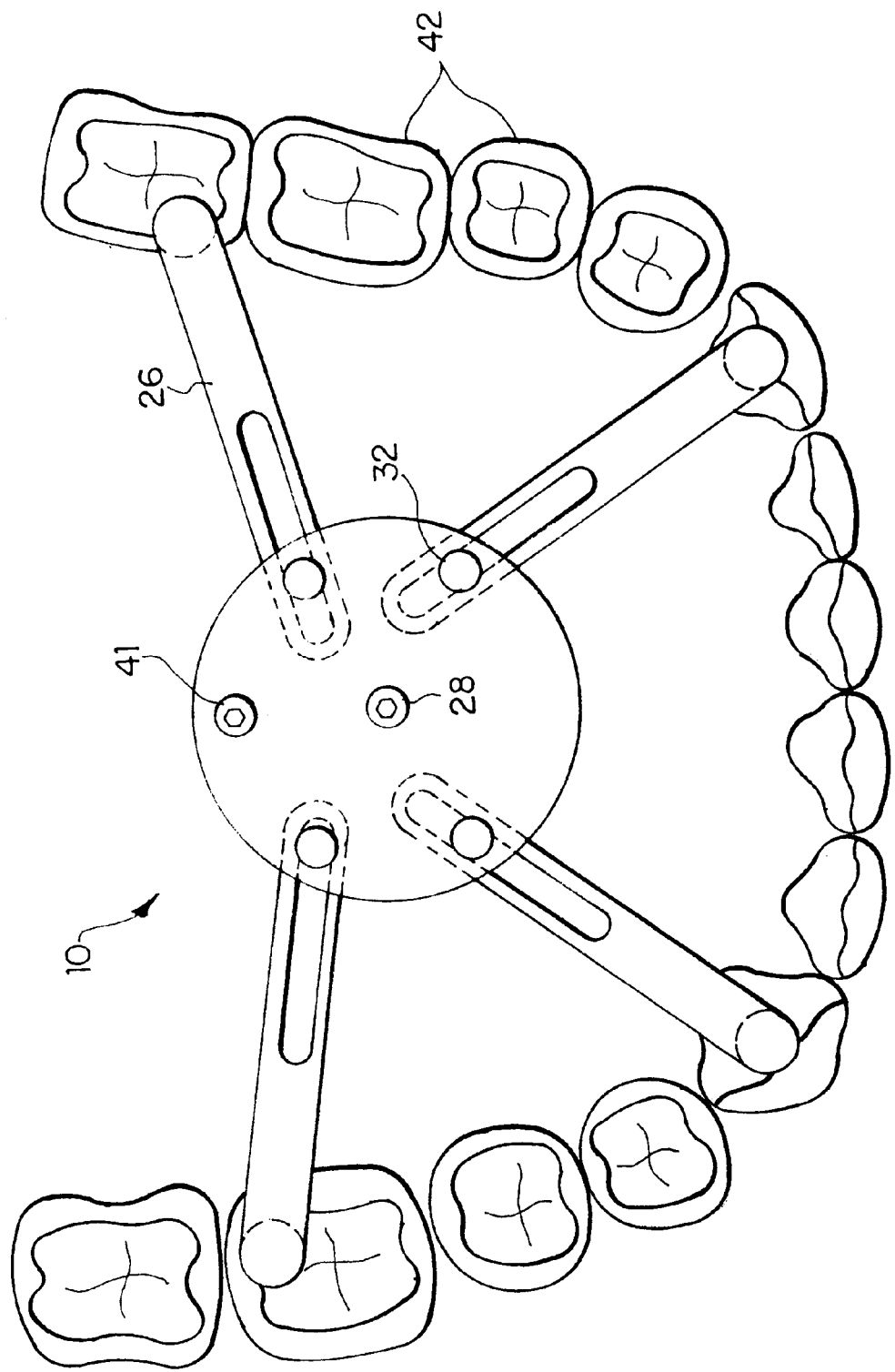

METHOD AND APPARATUS TO VERIFY DENTAL MODEL ACCURACY

FIELD OF INVENTION

This invention relates a device that verifies the accuracy of dental casts, which is both efficient and easy to use

BACKGROUND OF THE INVENTION

Dental impressions are taken to create molds of a persons dentition. These molds are either utilized as study models or used to fabricate various dental appliances by the dental professionals. The dental appliances fabricated include cast partial dentures, acrylic night guards, snore guards or other dental devices to fit the mouth.

Problems do arise when the finished dental product is delivered to the patient and does not fit the mouth. When this occurs, it is a very costly error. It is often time consuming for the dentist to adjust the prosthesis. After a given allotted time to adjust the appliance the dentist may elect to abandon the particular item and take new impressions to begin again. He must retrace his steps with the case and duplicate completed procedures. When this happens, the inventor feels that the dentist has made no profitable gain on the case.

The overhead of office chairtime and materials is costly. Besides this the dentist/laboratory relations suffer. Also, the dentist could have lost the confidence in the instance of a dubious patient. And worst of all, the second appliance may not fit. An ill-fitting appliance is detrimental to the mission of the dentist office.

Often, the origin for ill-fitting dental prostheses is error in model accuracy. To eliminate some of the frustration, the models engendered from the impressions must be verified for accuracy. Model verification is not now performed in the dental profession. Before time and effort is spent by the laboratory technicians in fabricating dental prostheses, model accuracy should be verified by the dentist.

In U.S. Pat. No. 386,004, inventor Eddy discloses a repair clamp for spectacles. The use for this device is to stabilize three different members. These members are pulled together into a specific relation and held in a clamp. The device is not used for measuring.

In U.S. Pat. No. 3,200,497, D. J. Goodfriend shows a method to transfer dental anatomical relations onto an articulator. This device relates three different points. It uses these points to align models on an articulator. It does not verify an exact measurement. Even if this device were used several times on the same individual three different measurements would be obtained.

In U.S. Pat. No. 1,385,070, Davison discloses a dental bite taking device. This device also takes a measurement in order to transfer information regarding relationships. This is used to set articulators; it is not used as an accuracy verifier.

OBJECTS AND ADVANTAGES

The object of this invention is to verify the accuracy of a dental model.

This has never been done in the dental profession. Indeed, the opposite is taught in many dental schools. It is widely held that no two models taken on the same individual will be exactly alike. This slight variation is observed at times. It is due to slight variations in impression accuracy as well as distortion during the setting of die material. However, with care, clinically exact working models are possible.

The philosophy that no two models can be alike is damaging to the concepts of the fabrication process. It discourages the application of a step to verify the trueness of a model. Verifying a model forces the practitioner to address the matter of impression taking. He can readily detect when models are inaccurate before the whole process is muddled by the complexities of laboratory work. When a dentist presently receives a fabricated appliance that needs much adjustment, he can only begin to guess where the errors originated. Sending a model to the laboratory that the dentist knows is accurate gives confidence and stability to the process.

This inventor holds that two clinically exact models can be made with accurate impression techniques. And no prosthesis fabrication should begin unless the models can be verified and proven accurate.

The inventor has high regards for the services of dentists and the supporting laboratory. The technician's talents can now be better utilized with accurate models. Impression materials, laboratory materials, office chair time, and a patient's time are all very dear. A remake due to an ill-fitting appliance is frustrating to all and adds needlessly to cost.

This disclosure is not obvious due to the fact that many cases performed with present day techniques do come out satisfactorily. Yet, very few are perfect.

Innate complexities of prosthesis fabrication mask the problems of any one separate step. The present flaws of impression taking are not obvious. Many feel that no two models are exactly alike. Because of this many clinicians would not consider verifying the accuracy of the casts.

Also, some dentists are unaware of the real costs associated with an ill-fitting prosthesis. Because of the above reasons, model verification has never been applied in dentistry. In this age of cost conscience health care, the process of making dental prostheses must be met with higher standards. Respect to detail and perfection will prevent needless duplication of steps due to inherent present flaws.

BRIEF DESCRIPTION OF DRAWING

FIG. 2 is a lateral view of assembled verifier.

FIG. 3 is a top view model verifier in place on dental cast

DETAILED DESCRIPTION OF THE INVENTION

Figure 1:
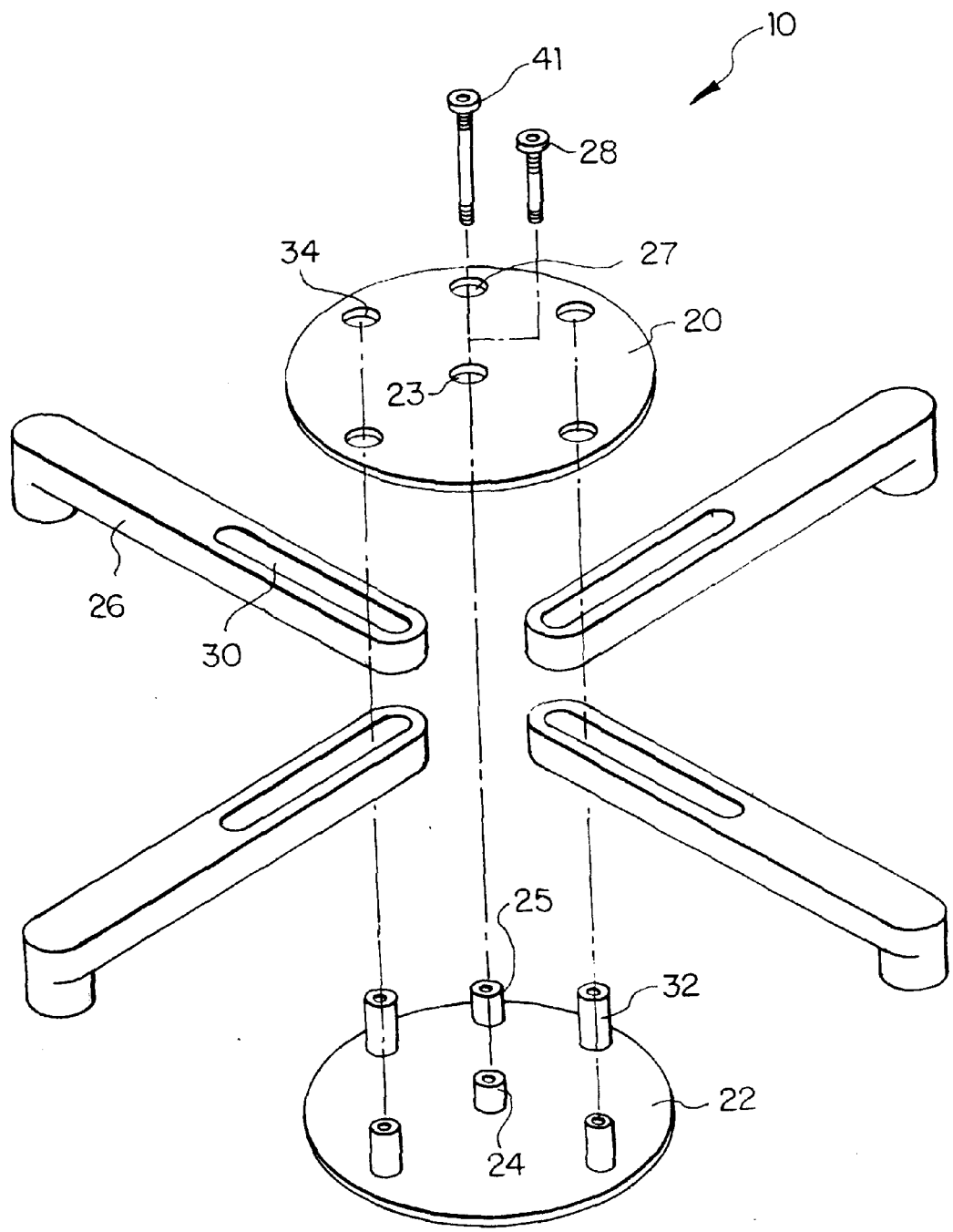
FIG. 1 is a lateral, exploded view of a model verifier.

The model verifier, 10, FIGS. 1, 2, and 3 has four adjustable arms, 26, FIG. 1. The verifier has an upper disc, 20 and a lower disc, 22. Near the periphery of the upper disc, 20 are four openings, 32 that mate with four opposing pins, 34 on the lower disc, 22. Between the two discs are four movable arms, 26 with slots, 30. The slots, 30 accommodate the passage of pins, 32 extending from the lower disc, 22 passing through the slots, 30 of arms, 26 and into the open cutouts, 34 of the upper disc, 20. The arms, 26 are able to reciprocate about the pins, 32 in an arc movement as well as in and out from the center. The four arms, 26 are locked in position, once an established format is determined, by a locking screw, 28.

In use, the dentist would first procure a study model of a patients dentition in preparation to begin fabrication of a cast partial denture. The study model is useful for the traditional reasons and is handled in usual manner. It is surveyed for a partial design and a custom tray is made. At this point, the model verifier, 10 is set. The locking screw, 28 is loosened enough for a friction fit movement of the four arms, 26. The rests, 39 of the arms are fitted over prominent dental cusps in four areas of the models, FIG. 3. The areas are cusp tips.

These would not usually be modified when teeth are prepared to receive a cast partial. These are the least likely to have air bubbles.

Once the position is determined for the arms of the modifier the holding screw, 28 passing through opening, 23 is tightened into threaded area, 24 of lower plate, 22 and the arms are locked. Accurate setting methylmethacrylate is then added to the rest areas, 39 of the arms and while the resin is still soft, the verifier is returned to the study model. The soft resin will take the shape of the coinciding cusp tips for which the verifier was set.

When the patient returns for the final impression, the model verifier is fitted over the same selected teeth that were chosen to set the verifier. A definitive seating would confirm the accuracy of the study model. The verifier is put aside to be used later.

If the modifier does not match the patients mouth, then there is a flaw in the study model. A drop of methylmethacrylate is added to areas of the rests that do not touch the teeth accurately. This could even mean adding material to all four rests. While the material is still soft it is returned to the mouth to register the shape of the chosen four cusps. Thus, an exact replication is recorded for the location of the four cusp tips.

The final impression is poured in the usual manner to yield a master model. Now, by similar congruent fit, the verifier is used to confirm the accuracy of the master model.

The verifier is sent with the master model to the dental laboratory. In the specific case of a cast partial, an interim refractory model is duplicated from the master model. At this point the technician can confirm the accuracy of his impression and resultant refractory model with the same adjusted verifier. The actual casting will be made on this refractory model.

In cases involving maxillary partials, a fifth point of orientation may be registered. An accessory screw, 41 may pass through the opening, 27 of the upper plate, 20 and turned into threaded opening, 25 of the lower plate, 22 to contact the palatal area.

CONCLUSIONS, RAMIFICATIONS AND SCOPE OF INVENTION

So it can be seen by the reader that the invention disclosed herein is an efficient dental instrument for confirming the accuracy of dental casts.

The verifier is easy to use. It can be set by ancillary personnel after training.

It is readily adjusted to fit any combination/variation of the dentition.

Once set, for a specific case, a single verifier has several applications along the fabrication process. It verifies the study model, the final model, and the refractory model.

The mission of the enclosed disclosure is to help dentists achieve the best possible results for their endeavors.

This method and apparatus disclosed are long overdue. Until the process of digital scanning is perfected and applied, the value of traditional elastomeric impression taking must be enhanced. The shortcomings can be circumvented.

The above disclosure gives order and greater significance to the fabrication process. This gives higher satisfaction to all involved. It offers a more predictable and profitable modality to the dental profession.

Having thus fully described the construction and combination or arrangement of the several parts of my invention, its advantages, and the manner of using the same, what I claim as new is:

1. A method for verifying the accuracy of dental casts comprising the steps of:

a. fabrication of two similar dental casts from impressions taken of selected dentition;

b. determine at least two points of reference to compare between said dental casts that are free of imperfections in the same areas on both casts;

c. make imprint of said points of reference on first cast by applying accurate hardening material directly to said points on said first cast;

d. record spatial relation of said added hardened material relative to said first cast by luting all said hardened material while it is still on said first cast to appropriately sized rigid structure;

e. transfer said hardened material combined with said attached rigid structure from said first cast to a second cast and confirm identical fit on said second cast as witnessed on said first cast.

2. An apparatus used to verify the accuracy of similar dental casts comprising:

first and second discs having facing planar surfaces held in a congruent relation with respect to one another by at least one set screw extending perpendicularly between the facing planar surfaces of said discs; said first disc having at least two spaced apart pins extending perpendicularly from the planar surface facing said second disc;

at least two elongated arms each having an inward end and an outward terminal end, said arms each having a slot extending along a length thereof at said inward end, each of said slots receiving one of said pins such that each of said arms may be moved longitudinally and rotationally with respect to the pin received in the arm's slot, wherein said arms may be fixed with respect to one another by moving said first and second discs toward one another with said set screw; and wherein said at least two arms extend in a sufficient length beyond the circumference of said discs that they may adjustably extend to allow said outward terminal ends of said arms to coincide to desired points of a dental cast.

\* \* \* \* \*